United States Patent [19]

Berndt

[11] Patent Number: 5,293,210
[45] Date of Patent: Mar. 8, 1994

[54] DETECTION OF BACTERIA IN BLOOD CULTURE BOTTLES BY TIME-RESOLVED LIGHT SCATTERING AND ABSORPTION MEASUREMENT

[75] Inventor: Klaus W. Berndt, Stewartstown, Pa.

[73] Assignee: Becton, Dickinson and Company, Franklin Lakes, N.J.

[21] Appl. No.: 874,252

[22] Filed: Apr. 24, 1992

[51] Int. Cl.$^5$ ............................................. G01N 33/48
[52] U.S. Cl. ..................................... 356/39; 435/34; 435/808; 356/338
[58] Field of Search ................. 356/39, 338, 441, 442; 435/34, 39, 40, 808

[56] References Cited

U.S. PATENT DOCUMENTS

| | | | |
|---|---|---|---|
| 4,152,213 | 5/1979 | Ahnell | 195/103.5 M |
| 4,516,858 | 5/1985 | Gelbwachs | 356/437 |
| 5,119,815 | 6/1992 | Chance | 356/39 |

OTHER PUBLICATIONS

K. Berndt, et al., "Picosecond laser spectroscopy with avalanche photodiodes," *SPIE-The International Society for Optical Engineering*, vol. 909 Time-Resolved Laser.

J. R. Lakowicz, et al., "Frequency-Domain Measurements of Photon Migration in Tissues," *Chemical Physics Letters*, (1990), vol. 166, No. 3, pp. 246-252.

Klaus W. Berndt, et al., "Phase-modulation fluorometry using a frequency-doubled pulsed laser diode light source," *Rev. Sci. Instrum.*, 61(7), Jul. 1990, pp. 1816-1820.

K. Berndt, "Opto-electronic high-frequency cross-correlation using avalanche photodiodes," *Measurement*, vol. 5, No. 4, Oct-Dec. 1987, pp. 159-166.

*Primary Examiner*—Richard A. Rosenberger
*Attorney, Agent, or Firm*—Alan W. Fiedler

[57] ABSTRACT

Methods and apparatus for detecting bacteria in samples using time-resolved light scattering and absorption measurement are disclosed. The present invention provides a system wherein a plurality of samples may be tested by providing a modulated excitation signal which is introduced into each sample and collected at a point disposed across each sample. The amplitude and phase of the collected signal are then processed to determine the time characteristics, modulation and phase of the signal after it has passed through the sample. By comparing time characteristics, modulation and phase with the time characteristics, modulation and phase collected at a previous point in time or alternatively from a sample known to be free of bacteria, the presence of bacteria may be determined, since it has been found that the presence of bacteria causes a significant change in the time characteristics, modulation and phase. Preferably, diode lasers are used to introduce modulated electromagnetic radiation into the samples and a multichannel plate photomultiplier tube is used to provide a signal from which the phase and amplitude can be determined. Alternatively, in other embodiments of the present invention the modulated electromagnetic radiation may be introduced using an optical switch and the multichannel plate photomultiplier tube may be replaced by avalanche photodiodes disposed against each sample that also create a signal containing time-averaged intensity, amplitude, and phase information.

33 Claims, 6 Drawing Sheets

DETECTION OF BACTERIA IN BLOOD CULTURE BOTTLES BY TIME-RESOLVED LIGHT SCATTERING AND ABSORPTION MEASUREMENT

The present invention relates to non-invasive methods and apparatus for detecting biological activities in a specimen such as blood by measuring the absorption and scattering of light, and in particular to systems wherein a specimen and culture medium are introduced into a sealable container and exposed to conditions enabling metabolic processes to take place and thereby permit the detection of the presence of microorganisms in the sample.

BACKGROUND OF THE INVENTION

Usually, the presence of biologically active agents in a patient's body fluid, and especially in blood, is determined using blood culture vials. A small quantity of blood is typically injected through an enclosing rubber septum into a sterile vial containing a culture medium. The vial is typically incubated at 37° C. and monitored for bacterial growth.

Common visual inspection for bacterial growth involves monitoring the turbidity of the liquid suspension. Known instrumented methods detect changes in the carbon dioxide content of the culture bottles, which is a metabolic by-product of the bacterial growth. Monitoring the carbon dioxide content can be accomplished by methods well-established in the art, such as radiochemical (e.g., BACTEC®, Becton-Dickinson, Franklin Lakes, N.J., U.S.A.), infrared absorption at a carbon dioxide spectral line (e.g., NR-BACTEC®, Becton-Dickinson, Franklin Lakes, N.J., U.S.A.), or pressure/vacuum measurement techniques such as those disclosed in U.S. Pat. No. 4,152,213—Ahnell. These methods, however, all require invasive procedures which result in the well-known problem of cross-contamination. As used herein, the term invasive describes a procedure wherein the sample container is opened, pierced or otherwise placed in communication with an external environment during the point at which the presence or absence of bacteria is determined.

Recently, non-invasive methods have been developed involving chemical sensors disposed inside the sample vial. These sensors respond to changes in carbon dioxide concentration by changing color or by changing fluorescence intensity. These techniques are based on light intensity measurements, thus errors occur if the light sources used to excite the sensors or the photodetectors used to monitor intensities show aging effects over time. Certain of the disadvantages of such intensity-based methods could be overcome by utilizing modulated excitation light in combination with fluorescent sensors that change their decay time with changing carbon dioxide concentration. In this case, intensity measurement is replaced with time measurement, and intensity changes have no impact. However, current fluorescent decay time sensors require high-brightness, short-wavelength light sources (550 nm or shorter) that are intensity-modulated at very high frequencies (typically above 100 MHz). An example of such a device would be a 5-mW green HeNe laser (543.5 nm) externally modulated by means of an acousto-optic light modulator. However, as well known by those of ordinary skill, the laser/modulator combination is rather expensive, requiring that the individual samples be moved to the laser instead of having one light source at each sample. Such an instrument would necessarily have a complicated mechanism for effecting the transportation of the individual samples, and the time interval between successive measurements for each sample would be relatively long. Since for the time being it appears unlikely that high-brightness, short-wavelength semiconductor diode lasers will be developed to permit a commercially feasible embodiment of this type of system, such an improved system would suffer serious practical shortcomings.

A need therefore remains to provide methods and apparatus for bacteria detection in blood culture samples non-invasively and in a commercially feasible manner. It is therefore an object of the present invention to provide methods and apparatus for detecting bacteria in a sample that permit a plurality of samples to be tested simultaneously in a rapid, effective and economical manner.

SUMMARY OF THE INVENTION

The present invention provides optical methods and apparatus for detecting biological activities in a sample that are non-invasive, not intensity-based, do not require chemical sensors or any other additives within the sample, do not require high-brightness, short-wavelength light sources, have no moving parts and allow an almost continuous monitoring of each sample vial.

The present invention provides methods for detecting the presence of bacteria in a sample by monitoring the time characteristics of modulated electromagnetic radiation that has migrated through the sample. The methods of the present invention preferably include the steps of introducing modulated electromagnetic radiation into the sample at a first point and receiving the collected radiation at a second point. The time-averaged intensity of the collected radiation over time is then determined, as well as the amplitude and phase of the collected radiation relative to the injected radiation. In accordance with the present invention, bacteria are present if the time characteristics of the collected radiation show changes over time.

In a preferred embodiment, a computer is provided with data indicative of the intensity of the collected radiation over time and the amplitude and phase of the collected radiation relative to the injected radiation. The computer calculates the modulation of the collected radiation, which is obtained by dividing the amplitude signal by the intensity signal. Since the measured amplitude is directly proportional to the intensity, the calculated modulation is independent of the intensity. Because the phase is also independent of the intensity, an instrument according to the present invention exhibits an excellent long-time stability.

The present invention determines the presence of bacteria in a plurality of samples by sequentially directing modulated electromagnetic radiation to each sample, sequentially introducing the modulated electromagnetic radiation into each sample at a first point and sequentially detecting the signal that emerges from the sample and thereby determining the presence of bacteria in each of the plurality of samples. The step of sequentially directing the modulated electromagnetic radiation may either be carried out using a multiplexer to sequentially excite a laser diode disposed adjacent each of the samples, or may be carried out by transmitting a modulated electrical signal to a laser thereby creating modulated electromagnetic radiation that is transmitted to each of the samples using an optical switch. Preferably, the determination of the time characteristics of the collected radiation over time either comprises the steps of transmitting the collected radiation to a multichannel plate photomultiplier to create a signal and measuring the amplitude of the signal or, alternatively, the collected radiation may be used to excite an avalanche photodiode that is used as a detector to create a photodiode output signal and the time characteristics of the photodiode output signal are measured.

The present invention also discloses apparatus for detecting the presence of bacteria in a sample comprising a light source, preferably a laser, for introducing modulated electromagnetic radiation into a sample at a first point and a detector for receiving collected electromagnetic radiation at a second point. A processor is provided for determining the intensity of the collected electromagnetic radiation over time, and a vector voltmeter is used to determine the amplitude and phase of the modulated radiation relative to the injected radiation. A computer preferably determines the modulation and phase of the collected radiation to detect the presence of bacteria. If bacteria are present, the time characteristics of the collected radiation will change over time.

The present invention also provides an improved optical switch for use in certain embodiments of the apparatus of the present invention to sequentially introduce modulated electromagnetic radiation into each of a plurality of samples. Preferably, the optical switch comprises a laser disposed to impinge a laser beam on a deflector, wherein the deflector focuses the laser beam upon one of a plurality of excitation fibers. The deflector is precisely moved such that the laser beam is sequentially focused upon each of the plurality of excitation fibers. In a preferred embodiment, the deflector is moved by a stepper motor to rotate the deflector about an axis.

A preferred form of modulated electromagnetic radiation is given by a sequence of periodic pulses with a wavelength within the range 600 nm to 900 nm, or more specifically, between 650 nm and 800 nm. This sequence of periodic pulses is equivalent to electromagnetic radiation that is modulated at the pulse repetition frequency and at harmonics thereof. For the sequence, a time-averaged intensity is defined, as well as an amplitude and phase at each of these frequency components. The detection electronics are preferably tuned to one particular frequency component. For large sample volumes, low-frequency components are appropriate. For small sample volumes, higher harmonic frequencies can be selected in order to obtain maximum bacterial detection sensitivity.

In order to detect bacterial growth according to the present invention, the time characteristics for the collected radiation in the time domain may also be monitored. As can be shown using basic principles of information theory, data measured in the time domain and data measured in the frequency domain (i.e., the phase and modulation of the light) are equivalent. In practice, however, frequency-domain instruments can be produced at lower cost.

DESCRIPTION OF THE PREFERRED EMBODIMENT

Figure 1:
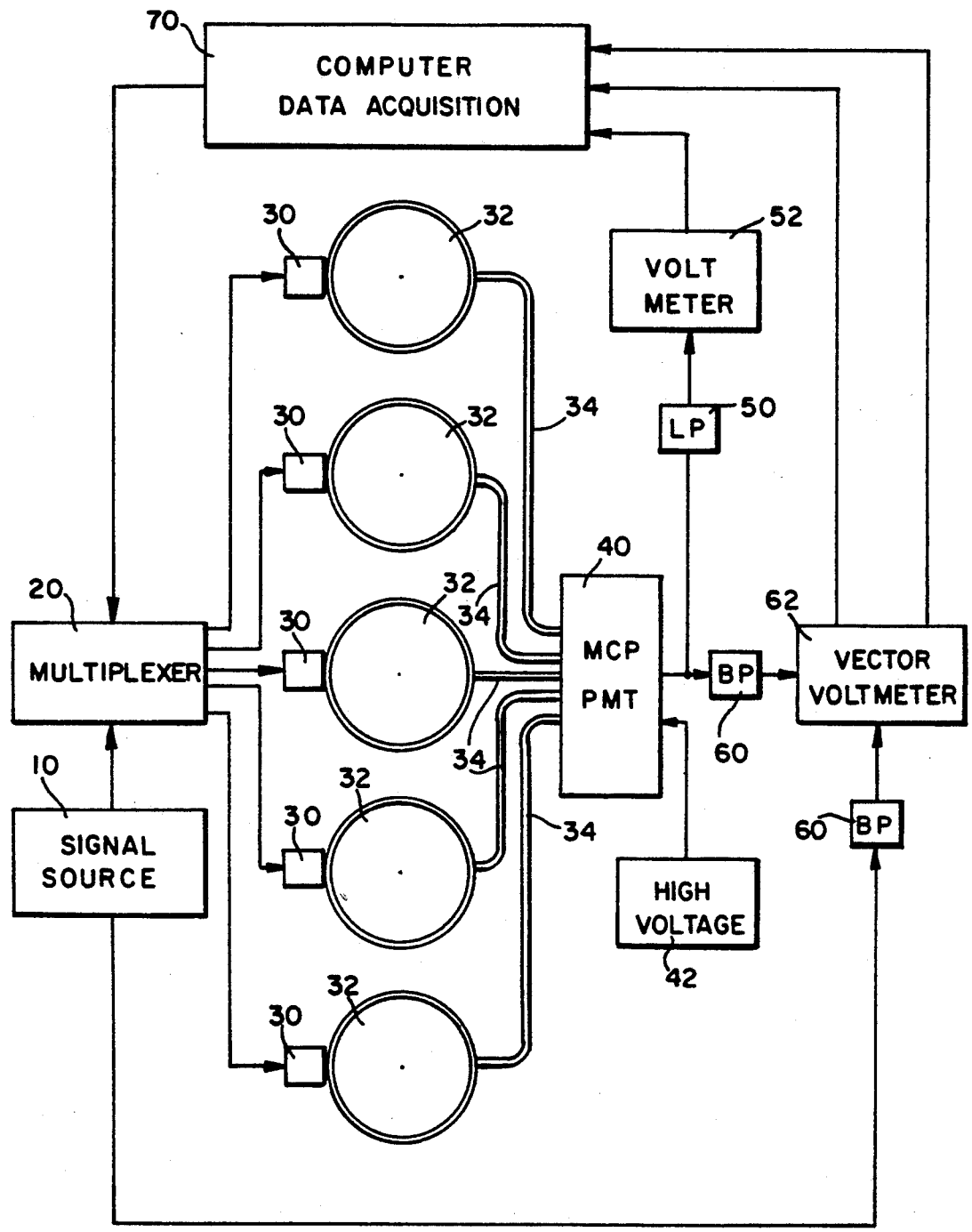
FIG. 1 is a schematic illustrating a first embodiment of the apparatus of the present invention.

A first embodiment of an apparatus made according to the present invention is shown in FIG. 1. A signal source 10 delivers periodic electrical sub-nanosecond electrical pulses to a multiplexer 20. The computer-controlled multiplexer 20 directs these periodic electrical pulses in a serial mode of operation to a plurality of diode lasers 30 for emitting light of a specified wavelength, each mounted closely to a sample container 32. Light reemerges from each sample container 32 and is collected at a small area approximately opposite the light injection area by a light collection means that is most preferably comprised of a fiber-optic bundle 34. The reemerging light is directed to a large-area multichannel-plate photomultiplier tube 40 which is powered by a high voltage source 42. The time-averaged output current of the photomultiplier tube 40 is measured by a low-pass filter 50 and a digital voltmeter 52. The voltage data are then stored within the memory of a computer 70. Two band-pass filters 60 and a high-frequency vector voltmeter 62 allow for determination of the high-frequency photocurrent signal amplitude and signal phase relative to the modulation phase of the diode lasers 30. As shown, a first band pass filter 60 receives a voltage signal from the output of the photomultiplier tube 40, while a second filter 60 is connected to the signal source 10. By combining these signals in the vector voltmeter 62, the amplitude and phase of the output are determined. These data are also stored in the memory of the data acquisition computer 70.

In operation, each diode laser 30 introduces ultrashort periodic electromagnetic radiation pulses into the sample container 32, which preferably contains a liquid blood culture suspension or other sample. The electromagnetic radiation is comprised of photons that migrate through the sample and experience multiple scattering and absorption events. Due to these multiple events, the photon path length within the medium is not a discrete one, but can instead be described as a distribution of path lengths. In other words, the reemerging light pulse is much longer than the pulse that was introduced. The pulse shape and the pulse duration will depend on the absorption coefficient, $\mu_A$, and on the scattering coefficient, $\mu_S$, of the blood culture or other sample. If bacteria are present and are consuming oxygen, the hemoglobin oxygenation of the blood will be reduced. In the case of other samples, other oxygen bearing species will be reduced. Reduced oxygenation is known to increase the hemoglobin absorption within the spectral range of about 600 nm to 800 nm. An increasing absorption should result in shorter pulses of electromagnetic radiation because the photon "lifetime" within the medium will be shortened. On the other hand, an increasing number of bacteria is expected to increase the scattering efficiency. Therefore, a change in both absorption and scattering during bacterial growth is expected.

Figure 4:
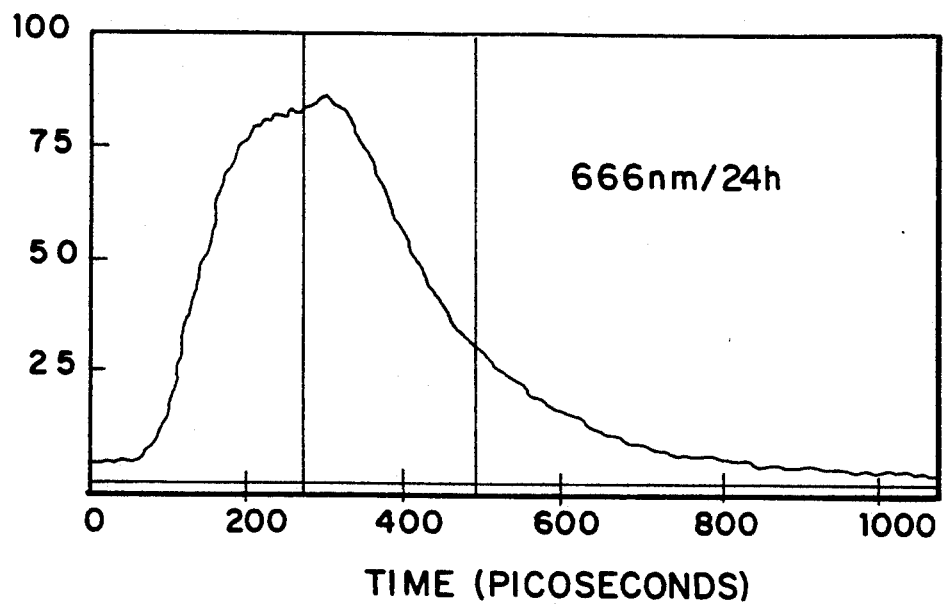
FIG. 4 presents a plot of the collected signal intensity vs. time for a control sample measured using a synchroscan streak camera as a photodetector.
Figure 5:
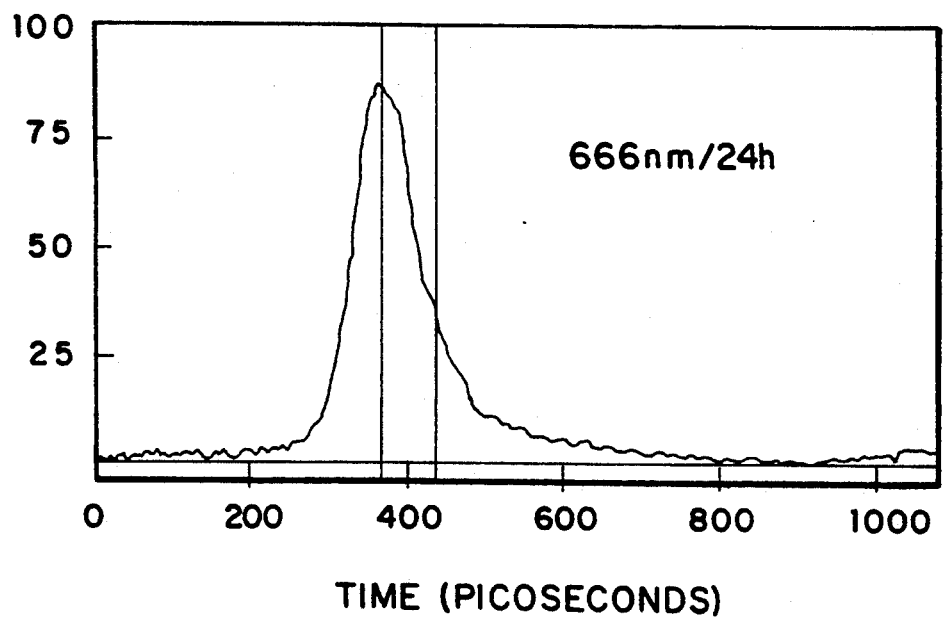
FIG. 5 is a plot similar to FIG. 4 obtained from a sample inoculated with E. Coli bacteria.

It has now been found that the detection of bacterial growth can be accomplished using a frequency-domain system which analyzes the time characteristics of the collected electromagnetic radiation directly. In general, time-domain data are more vivid. Therefore, some experimental time-domain data are presented to illustrate the underlying principles of the present invention. Using a Hamamatsu synchroscan streak camera with 10 ps time resolution as a sensitive high-speed photodetector, two corresponding plots for a 666 nm wavelength signal were obtained and are shown in FIGS. 4 and 5. The plot in FIG. 4 shows the measured light output waveform for a BACTEC ® 6A blood culture medium (Becton-Dickinson, Franklin Lakes, N.J., U.S.A.) and blood in a typical BACTEC ® vial having a 43 mm outer diameter after 24 hours of incubation. It will be observed that the electromagnetic radiation decay time in this case is about 196 ps. FIG. 5 illustrates the results obtained from a similar vial under identical conditions that was inoculated with about 100 cfu per ml of E. coli bacteria. As can be seen, this vial shows a significantly shorter waveform with a decay time of only about 71 ps. More data are presented in Table 1 where the measured decay time is given for two different wavelengths and at two different output positions relative to the injection area, characterized by the angle between the source and the detector, i.e., 180° indicates that the detector is positioned directly across from the source:

TABLE 1

| Sample | Wavelength (nm) | Angle (degrees) | Decay Time (ps) |
|---|---|---|---|
| 6A Control | 627 | 90° | 125 |
| 6A E. coli | 627 | 90° | 35 |
| 6A Control | 666 | 90° | 117 |
| 6A E. Coli | 666 | 90° | 47 |
| 6A Control | 666 | 180° | 196 |
| 6A E. coli | 666 | 180° | 71 |

These data were obtained using the above-described equipment in order to evaluate the theoretical basis for the present invention. It will be understood, therefore, that the decay times measured and reported are for purposes of comparison and for verifying the operation of the present invention.

In an instrument made in accordance with the present invention, time characteristics are detected by using either time-domain or frequency-domain principles. In terms of cost, the latter are more advantageous. As known by those of ordinary skill, time characteristics can be monitored by using the phase shift method or the demodulation method. In both cases, maximum decay time resolution would be obtainable under the condition $\omega\tau \simeq 1$, where $\omega = 2\pi f$ is the circular light intensity modulation frequency, and $\tau$ is the decay time for a control sample. Thus, assuming a decay time of 200 picoseconds, an optimum light modulation frequency of about 800 MHz results. At present, multichannel-plate photomultipliers would be required in order to detect the 800-MHz light modulation. Therefore, as shown in FIG. 1, an apparatus made in accordance with the present invention can be constructed using a multichannel plate photomultiplier tube 40. Unfortunately, these detectors are still relatively very expensive. However, if fibers 34 of about 1 mm diameter are assumed, a commercial multichannel plate photomultiplier tube with a typical photocathode diameter of 18 mm (Hamamatsu, Model R2809U, Hamamatsu Electronics, Bridgewater, N.J., U.S.A.) would accommodate up to 254 fibers, and would therefore permit the construction of an instrument capable of monitoring 254 sample containers at one time. Therefore, the detector cost per vial would be acceptably low.

Those of ordinary skill will appreciate that the term time characteristics covers many of the possible properties of a pulse of light. When a light pulse is introduced into a scattering and absorbing medium, there are numerous properties related to the time course of the light that traverses the medium and reemerges. In general, the intensity increases to a maximum value and decays exponentially. In such a system numerous properties that reflect the information contained in this behavior can be measured. For example, the rise time of the pulse, the full pulse width and the delay time are all time characteristics that might contain useful information. However, for purposes of the present invention, two time characteristics—phase and modulation—are preferably measured and used to determine whether bacteria are present. However, although the methods and apparatus described herein use phase and modulation data, operable embodiments of the present invention that utilize other time characteristics can be devised.

Figure 6:
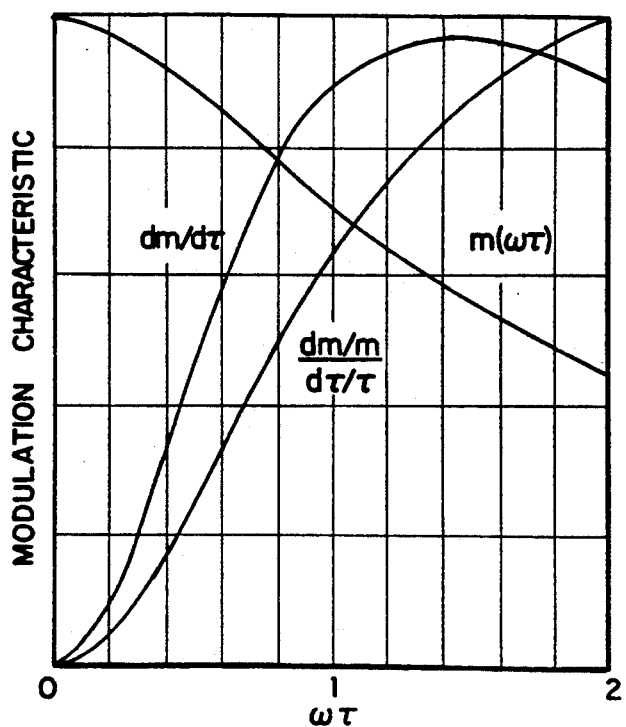
FIG. 6 illustrates the relationship between frequency-domain and time-domain characteristics.

In order to estimate the expected loss in decay time resolution at frequencies lower than the optimum modulation frequency, it must be assumed that the modulation degree, m, can be described approximately by the equation:

$$m(\omega\tau) = m_{DL}[1 + (\omega\tau)^2]^{-\frac{1}{2}}$$

where $m_{DL}$ is the diode laser modulation degree. This equation can be used to calculate the absolute change $dm/d\tau$ and the relative change $(dm/m)(d\tau/\tau)$. The relevant modulation characteristics are shown as a function of $\omega\tau$ in FIG. 6. It can be seen that optimum resolution is obtained at $\omega\tau > 1$, but even at $\omega\tau = 0.3$ there is still a reasonable amount of resolution available. Moreover, the plots in FIGS. 4 and 5 indicate that bacterial growth results in rather significant values of $d\tau/\tau$. Therefore, diagnostic instruments made in accordance with the present invention can be built using less expensive photodetectors since the sensitivity of the detector does not have to be as high as that of a photomultiplier tube.

Figure 2:
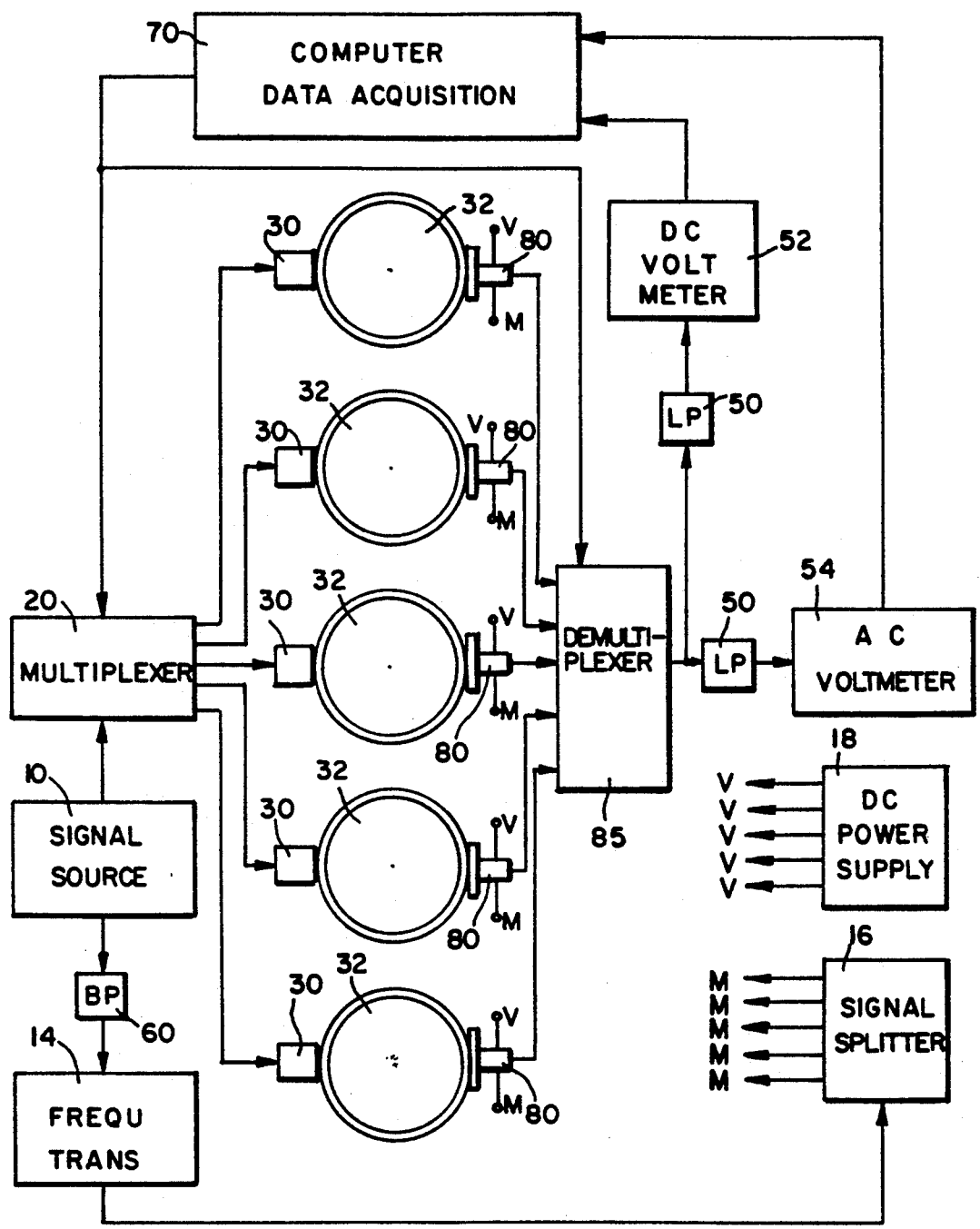
FIG. 2 is a schematic of an alternate embodiment of the apparatus of the present invention that uses a demultiplexer in place of the multichannel plate photomultiplier tube shown in FIG. 1.

One possible alternative embodiment to the apparatus of the present invention that uses a multichannel plate photomultiplier tube 40 as illustrated in FIG. 1 is shown in FIG. 2, where silicon avalanche photodiodes 80 are used as detectors. Except as noted herein, the apparatus of the embodiment of the present invention shown in FIG. 2 is similar to that described with reference to FIG. 1. Thus, like reference numerals will designate like components. In order to achieve high speed and high detectivity, the avalanche photodiodes 80 are operated as optoelectronic cross-correlators with a DC output signal. See Berndt, K. "Opto-electronic high-frequency cross-correlation using avalanche photodiodes," *Mea-*

*surement*, Vol. 5, No. 4, Oct.-Dec. 1987, pp. 159-166; Berndt, K., et al., "Picosecond laser spectroscopy with avalanche photodiodes," *SPIE*, Vol. 909 Time-Resolved Laser Spectroscopy in Biochemistry (1988), pp. 209-215, both of which are incorporated herein by reference as if set forth in their entireties.

Figure 3:
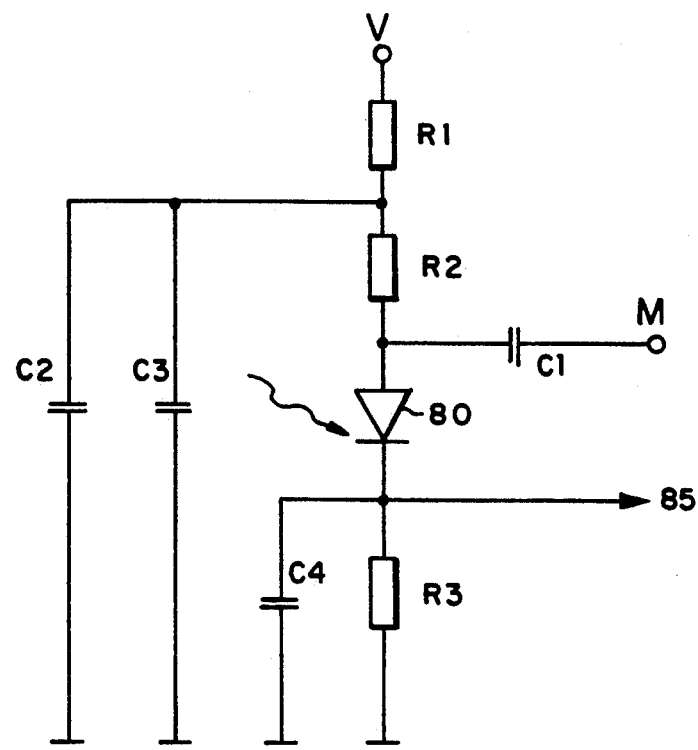
FIG. 3 is a schematic of a circuit that forms part of the detector preferably used in the apparatus of FIG. 2.

As shown in FIG. 2, part of the output of the signal source 10 is directed to a band-pass filter 60 where a particular harmonic of the repetition frequency is selected. A frequency translator 14 such as a synthesizer or single sideband modulator generates a frequency-shifted signal, preferably at an offset of about 50 to 100 Hz. This frequency-shifted modulation signal is divided into a plurality of modulation signals M using a signal splitter 16 and then added to the bias voltage of each of the avalanche photodiodes 80 at each junction M shown on each photodiode 80. The connection between each junction M and the signal splitter is not shown for purposes of clarity. It will be understood, however, that each signal M transmitted from the signal splitter 16 is equal to the others and is connected to one of the junctions M in a one-to-one correspondence. A DC power supply 18 similarly provides an appropriate voltage V to each junction V shown on each photodiode 80. These connections are also not shown for purposes of clarity, however, the same voltage V is provided to each avalanche photodiode 80. Details of the circuitry of the avalanche photodiode 80 are shown in FIG. 3, which is explained below. Adding the modulation signal M to the DC bias voltage V results in a gain modulation. Thus, the avalanche photodiodes 80 act as optoelectronic mixers with an additional DC signal proportional to the received average optical input power.

The intermediate frequency (IF) output of the photodiodes 80 has a frequency equal to the offset frequency generated by the frequency translator 14 and is fed to a low-frequency demultiplexer 85. Due to the relatively low frequency IF output, the equivalent noise bandwidth is very low when compared with direct detection high-speed photodetectors. Therefore, excellent detectivity is obtained. The IF signal carries all the high-frequency information of the optical signal received by the avalanche photodiodes 80. By separating the DC and the IF component using appropriate low pass filters 50 and measuring both with appropriate voltmeters 52,54, the modulation degree of the optical signal can be calculated and stored within the data acquisition computer 70.

Further details of the circuitry of the avalanche photodiodes 80 are illustrated in FIG. 3. The voltage input V from the DC power supply 18 is connected to a portion of the circuit comprising R1, R2, C2 and C3. The resistors R1 and R2 have values of about 10,000 and 50 Ohms respectively, while capacitors C2 and C3 have values of about 100 and $1 \times 10^{-9}$ farads respectively. The modulation signal M from the splitter 16 shown in FIG. 2 is connected to junction M shown in FIG. 3. A capacitor C1 having a value of about $1 \times 10^{-9}$ farads is disposed between the junction M and the photodiode 80. The output of the photodiode is connected to a capacitor C4 that has a value of about $10 \times 10^{-9}$ farads and a resistor R3 of about $1 \times 10^6$ Ohms, and the resulting output signal is connected to the demultiplexer 85 shown in FIG. 2. These values represent preferred values for each of the noted components. Those of ordinary skill will realize that one or more of these values may be altered, but that such alteration will necessarily result in different requirements for other components if the same output signal is to be obtained.

Apparatus made in accordance with the present invention does not require a particular diode laser pulse shape. After-pulses or any kind of pulse ringing have no negative impact on the decay time measurement process. The present invention requires only a stable light waveform at a constant repetition frequency. The band-pass filters 60 shown in FIGS. 1-2 select only one particular harmonic of the repetition frequency of the diode lasers 30. The modulation degree and/or the phase shift are derived using this frequency. This feature of the invention allows use of low-cost diode lasers.

As explained above, a wavelength within the range of about 600 nm to about 900 nm would be appropriate for detecting bacteria in a sample of blood and a wavelength between about 650 nm to 800 nm is preferred. At present, a variety of diode lasers for the range 670 nm to 800 nm are commercially available. Other types of light sources may also be used, however, the high frequency required results in a laser being the preferred light source. In any embodiment, an important aspect of the present invention is that it has now been discovered that bacterial growth can be monitored by introducing modulated electromagnetic radiation into a sample such as a culture medium/blood suspension and performing a time-resolved analysis of the reemerging light at a small area a known distance away from the injection area.

The main disadvantage of methods based on simple non-time-resolved intensity measurements is that they yield only one piece of information. Therefore, a change in the intensity of the reemerging light could be caused by light source aging, surface contamination, detector aging, geometry changes such as vial displacement, vial-shape and vial-size changes, or, finally, by bacterial activities. Except for light source aging, there is no practical way to detect these sources of error. However, in the case of time-resolved analysis, more than one parameter of the reemerging light is measured using the same photodetector under identical optical conditions—including all the sources of error mentioned above. Therefore, these sources of error are cancelled out. The only remaining change is related to the sample under test, e.g., the growth of bacteria in blood culture.

As is known to those of ordinary skill in the art, studies have been performed on time-resolved photon migration in living tissues. These studies have shown that the decay time of the reemerging light in tissue does not depend critically on the distance between optical input and optical output. See, for example, Lakowicz, J. R., Berndt, K. W., and Johnson, M. L., "Photon migration in scattering media and tissue," SPIE, Vol. 1204 *Time-Resolved Laser Spectroscopy in Biochemistry II* (1990), pp. 468-479. This means that the present invention measures the internal property of the blood culture and not a geometry or device property. In other words, the use of time-resolved spectroscopy by the present invention is a step towards an absolute detection system. The present invention therefore provides optical methods and apparatus for detecting biological activities in blood culture bottles, that is non-invasive, not intensity-based, does not require chemical sensors or any other additives within the blood culture vial, does not require high-brightness short-wavelength light sources, has no moving parts and allows an almost continuous monitoring for each vial.

Figure 7:
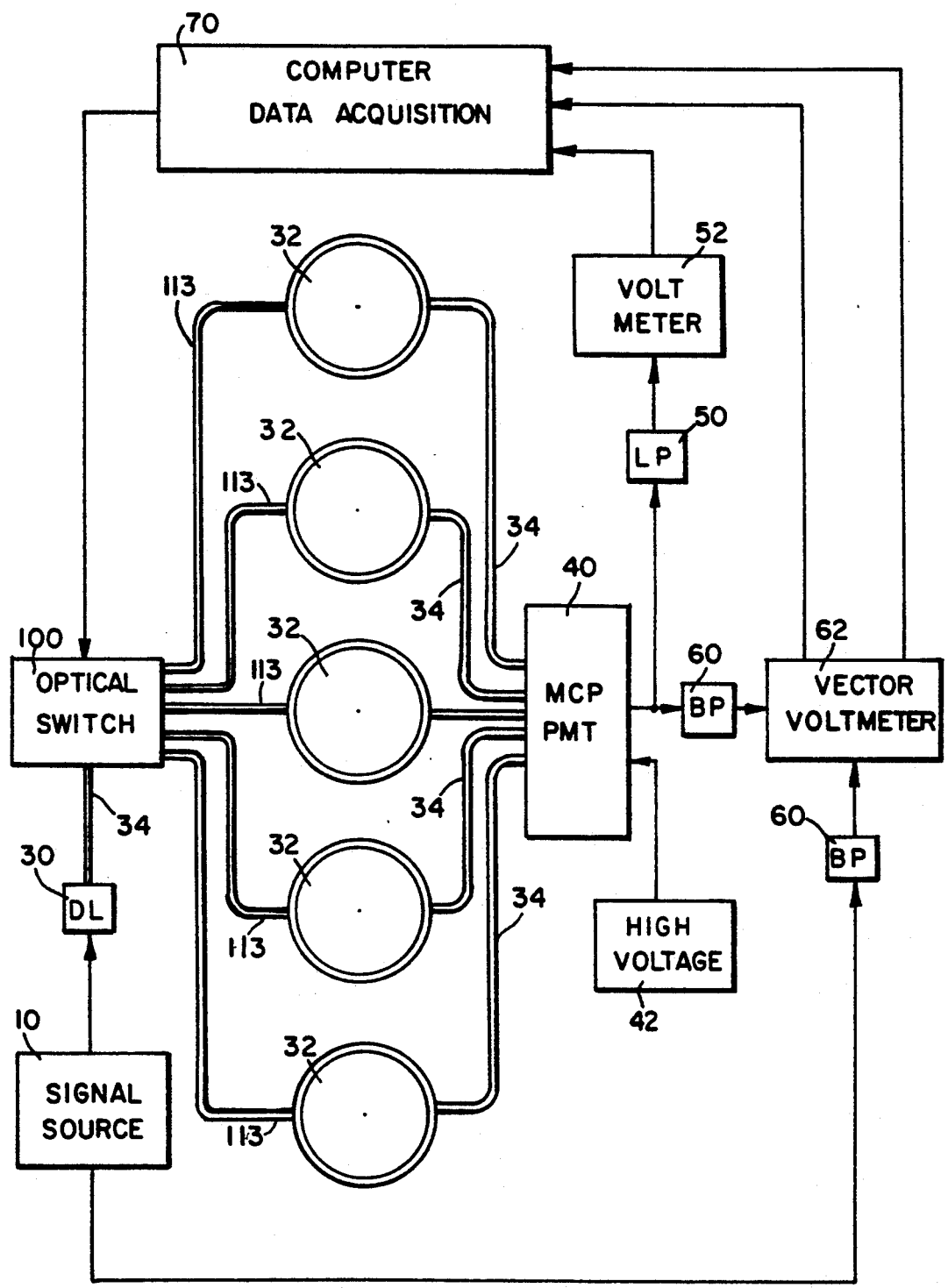
FIG. 7 is a schematic of another alternate embodiment of the apparatus of the present invention that uses an optical switch in place of a multiplexer shown in FIGS. 1 and 2.

Another alternate embodiment of the apparatus of the present invention is shown in FIG. 7. As before, like numerals designate like elements described above with reference to FIGS. 1 and 2. The optical output of a diode laser 30 is coupled via an optical fiber 34 to the input of an optical switch 100. This switch 100 contains a large number of optical output channels. Each output channel of the optical switch 100 is fed via an excitation fiber 113 to a sample container 32 and introduces modulated electromagnetic radiation into the sample. In a most preferred embodiment, the sample containers 32 contain blood culture medium and a blood sample. The optical switch 100 is preferably controlled by a computer 70 and in operation, the optical switch 100 directs the modulated electromagnetic radiation serially through the excitation fibers 113 to the sample containers 32. The detection of light reemerging from the sample containers 32 is preferably performed in the same way as shown and as described above with reference to FIG. 1 using a plurality of fiber optic bundles 34. As will be realized by those of ordinary skill, the fiber-optic coupling 34 between the diode laser 30 and the optical switch 100 is one possible embodiment. It is, however, a preferred embodiment because diode lasers 30 that include fiber-optic pigtail connectors are currently commercially available.

Another embodiment of the apparatus disclosed in FIG. 7 provides a system wherein the photomultiplier tube 40 and its associated processing equipment are replaced by the avalanche photodiodes 80, demultiplexer 85 and associated processing equipment as discussed above with reference to FIG. 2.

Figure 8:
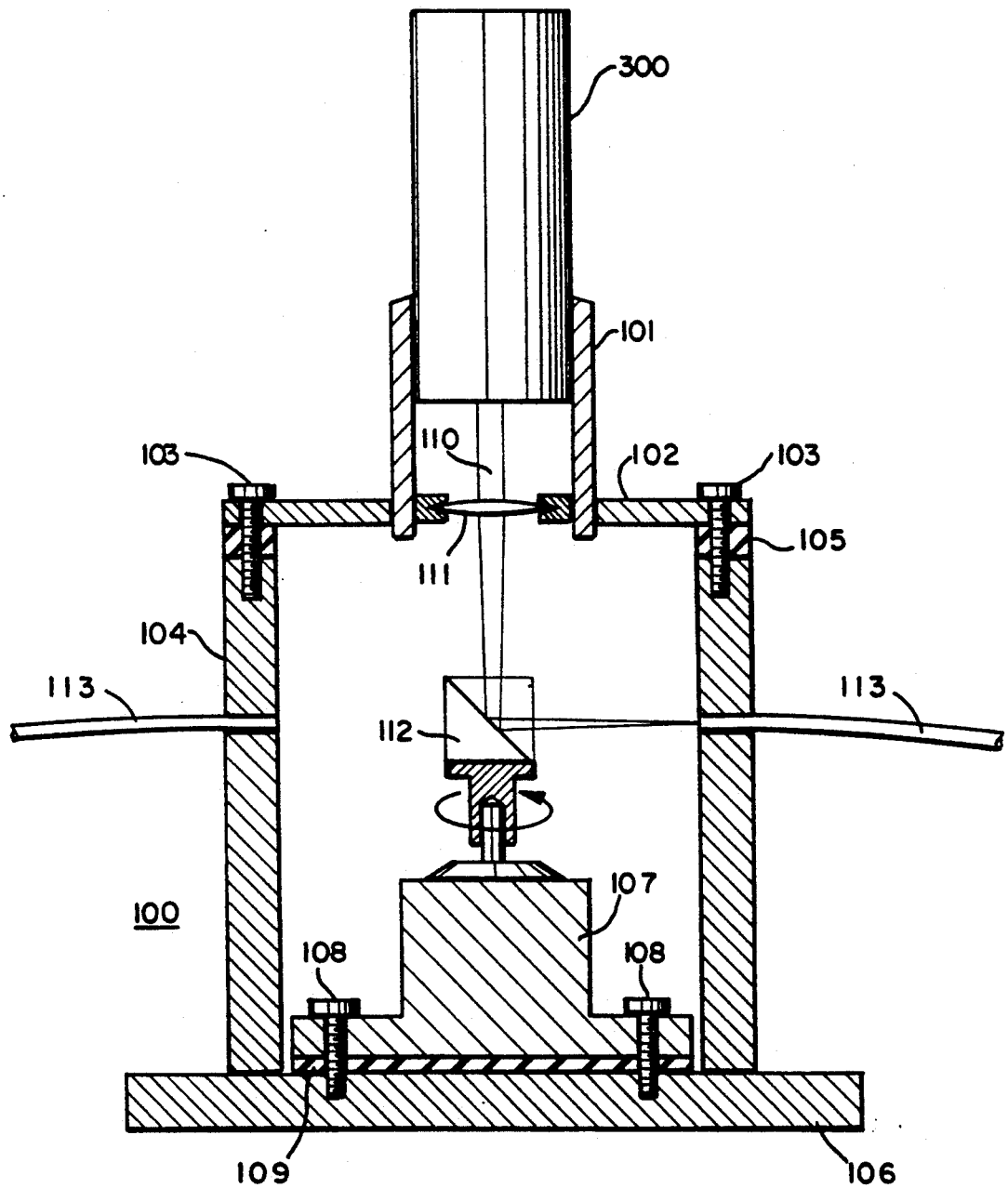
FIG. 8 is a cross-sectional elevation view of a preferred embodiment of an optical switch for use in the apparatus of FIG. 7.

In addition to the fiber-optic coupling 34 to the optical switch 100 described with reference to FIG. 7, an embodiment of the optical switch 100 is illustrated in FIG. 8 wherein a laser 300 is directly mounted to the optical switch 100. This direct-coupling provides compactness and a simple design. As shown in FIG. 8, a laser 300 is fixed to a mounting tube 101 which is in turn mounted to a plate 102, that is attached to a cylindrical housing 104 by several screws 103. A flexible portion 105 is preferably disposed between the plate 102 and the second cylinder 104 to allow for fine angular adjustment of the laser beam 110 with respect to a cylindrical housing 104 by the degree to which the flexible portion 105 is compressed. The second cylinder 104 is fixed to a base plate 106, upon which an electric stepper motor 107 is mounted coaxially with respect to the cylindrical housing 104. Fine angular adjustment of the stepper motor 107 is accomplished in a similar manner to that described above by providing several screws 108 and an additional flexible insert 109 disposed between the base plate 106 and the stepper motor 107. As shown, the laser beam 110 impinges upon a 90-degree beam deflector 112 mounted to the stepper motor shaft. Most preferably a movable lens 111 slidably mounted inside the mounting tube 101 allows for exact focussing of the laser beam 110 on the inputs of the plurality of excitation fibers 113 that are mounted in equidistant axial bore-holes along the perimeter of the cylindrical housing 104 after it strikes the deflector 112.

In operation, the computer-controlled stepper motor directs the full optical laser power serially toward each of the inputs of the excitation fibers 113. An optical switch of this design can easily accommodate 360 or more excitation fibers 113 by employing standard stepper motors. The optical switch 100 illustrated in FIG. 8 also allows for random access operation. It will be realized, however, that it is advantageous to use at least one optical output to establish a reference address.

The mechanical optical switch 100 described above with reference to FIG. 8 represents one embodiment of such a device that would be useful in certain embodiments of the apparatus of the present invention such as that illustrated in FIG. 7. Those of ordinary skill will realize, however, that there are a number of alternative ways by which a single laser beam 110 may be selectively time-shared with a plurality of excitation fibers 113. For example, a carriage containing the laser 300 could be advanced by a power screw or stepper motor to travel precisely along a linear array of excitation fibers 113 and achieve the same effect.

Thus, the present invention provides methods for detecting the presence of bacteria in a sample by monitoring the time characteristics of modulated electromagnetic radiation that has migrated through the sample. The detection principle of the present invention is based on the change in the time characteristics, modulation (i.e., amplitude/time-averaged intensity) and phase of the collected modulated radiation during bacterial growth. Since the time characteristics for a control (a sample without bacteria) do not change, a control sample is not required in all embodiments. Thus, a response such as that shown in FIG. 4 is typical of the response of a certain vial a short time after incubation, while FIG. 5 illustrates a response in the same vial after a time sufficient to permit bacteriological activity.

The methods of the present invention include the steps of introducing modulated electromagnetic radiation into a sample at a first point and receiving collected electromagnetic radiation at a second point. As noted above, it is preferred that the second point be located across from the first point, however, it will be understood that these two points need not necessarily be disposed directly opposite each other. The intensity of the collected radiation over time is then determined along with the amplitude and phase of the modulated radiation relative to the injected radiation. As noted above and pointed out with reference to FIGS. 4-5 bacteria are present if the time characteristics change over time. Preferably, the methods of the present invention include the steps of transmitting data indicative of the intensity of the collected radiation over time and the amplitude and phase of the radiation relative to the injected radiation to a computer and the computer carries out the steps of determining the modulation and phase of the collected radiation.

Although certain embodiments of the present invention have been set forth with particularity, those of ordinary skill will realize that numerous variations, adaptations and modifications of the invention disclosed herein are possible. Accordingly, the appended claims should be reviewed to determine the scope of the present invention.

What is claimed is:

1. A method for detecting the presence of bacteria in a scattering and/or absorbing sample comprising the steps of:
    introducing modulated electromagnetic radiation into the sample at a first point;
    receiving collected modulated electromagnetic radiation at a second point;
    determining a time-average intensity of the collected modulated electromagnetic radiation over time;

determining an amplitude of the collected modulated electromagnetic radiation relative to the introduced modulated electromagnetic radiation;

determining a modulation degree of the collected modulated electromagnetic radiation relative to the introduced modulated radiation;

comparing the determined modulation degree of the collected modulated electromagnetic radiation with a modulation degree measured at a prior time to detect the presence of bacteria; and indicating that bacteria are present in the sample if the determined modulation degree is significantly different than the modulation degree measured at the prior time.

2. The method of claim 1, further comprising the step of transmitting data indicative of the time-averaged intensity of the collected modulated electromagnetic radiation over time and the amplitude of the collected electromagnetic radiation relative to the introduced modulated electromagnetic radiation to a computer, wherein at least the step of determining the modulation degree of the collected modulated electromagnetic radiation and comparing the determined modulation degree with the modulation degree measured at the prior time are carried out by the computer.

3. The method of claim 1, wherein the step of introducing modulated electromagnetic radiation comprises the step of exciting a diode laser using a modulated driving signal to generate the introduced modulated electromagnetic radiation.

4. The method of claim 3, wherein the step of determining the amplitude of the collected modulated electromagnetic radiation relative to the introduced modulated electromagnetic radiation comprises the step of transmitting the collected modulated electromagnetic radiation to a vector voltmeter, and measuring the amplitude of the collected modulated electromagnetic radiation.

5. The method of claim 3, where the step of determining the time-averaged intensity and the amplitude of the collected modulated electromagnetic radiation relative to the introduced modulated electromagnetic radiation comprises the steps of:

transmitting the modulation driving signal to a frequency translator to generate a frequency-shifted signal;

adding the frequency-shifted signal to a bias voltage of an avalanche photodiode to create an output signal;

transmitting the output signal to an AC voltmeter and a DC voltmeter; and measuring a time-average intensity value and an amplitude value of the output signal.

6. The method of claim 5, wherein the step of determining the modulation degree of the collected modulated electromagnetic radiation comprises at least dividing the amplitude value by the time-averaged intensity value.

7. The method of claim 1, wherein the step of determining the intensity of the collected modulated electromagnetic radiation over time comprises transmitting the collected modulated electromagnetic radiation to a multichannel plate photomultiplier to create a current signal; and measuring an amplitude of the current signal.

8. The method of claim 1, wherein the step of determining the time-averaged intensity of the collected modulated electromagnetic radiation over time comprises exciting an avalanche photodiode using the collected modulated electromagnetic radiation to create a photodiode output signal; and measuring a time-averaged intensity value and an amplitude value for the photodiode output signal.

9. The method of claim 1, wherein the presence of bacteria is determined in a plurality of samples, further comprising the steps of sequentially directing modulated electromagnetic radiation into each sample; sequentially introducing modulated electromagnetic radiation into each sample at a first point; and sequentially detecting the presence of bacteria in each of the plurality of samples.

10. The method of claim 9, wherein the step of sequentially directing modulated electromagnetic radiation into each sample comprises the steps of transmitting a modulated signal to a multiplexer; and sequentially exciting a laser diode disposed adjacent each of the plurality of samples.

11. The method of claim 9, wherein the step of sequentially directing modulated electromagnetic radiation into each sample comprises the steps of transmitting a modulated signal to a laser to create modulated electromagnetic radiation; and sequentially transmitting the modulated electromagnetic radiation to each of the plurality of samples using an optical switch.

12. A method for detecting the presence of bacteria in a scattering and/or absorbing sample comprising the steps of:

introducing modulated electromagnetic radiation into the sample at a first point;

receiving collected modulated electromagnetic radiation at a second point;

determining a time-averaged intensity of the collected modulated electromagnetic radiation over time;

determining a phase of the collected modulated electromagnetic radiation relative to the introduced modulated electromagnetic radiation;

determining a phase shift of the collected modulated electromagnetic radiation relative to the introduced modulated electromagnetic radiation;

comparing the determined phase shift of the collected modulated electromagnetic radiation with a phase shift measured at a prior time to detect the presence of bacteria; and indicating that bacteria are present in the sample if the determined phase shift is significantly different than the phase shift measured at the prior time.

13. A method for detecting the presence of bacteria in a scattering and/or absorbing sample comprising the steps of:

introducing modulated electromagnetic radiation into the sample at a first point;

determining a modulation degree of the modulated electromagnetic radiation reemerging at a second point;

comparing the determined modulation degree with a modulation degree measured at a prior time to detect the presence of bacteria; and indicating that bacteria are present if the determined modulation degree is significantly different that the modulation degree measured at the prior time.

14. A method for detecting the presence of bacteria in a scattering and/or absorbing sample comprising the steps of:

introducing modulated electromagnetic radiation into a sample at a first point at an initial time;

receiving collected modulated electromagnetic radiation at a second point located across the sample from the first point;

determining a time-averaged intensity of the collected modulated electromagnetic radiation over time;

determining an amplitude of the collected modulated electromagnetic radiation relative to the introduced electromagnetic radiation;

determining a modulation degree of the collected modulated electromagnetic radiation;

repeating the steps or receiving collected modulated electromagnetic radiation, determining the time-averaged intensity, determining the amplitude and determining the modulation degree of the collected modulated electromagnetic radiation;

comparing the modulation degree measured at the initial time and at subsequent times to detect the presence of bacteria; and indicating that bacteria are present if the modulation degree of the sample measured at subsequent times is significantly different than the modulation degree measured at the initial time.

15. Apparatus for detecting the presence of bacteria in a scattering and/or absorbing sample comprising:

means for introducing modulated electromagnetic radiation into the sample at a first point;

detector means for receiving collected modulated electromagnetic radiation at a second point;

processing means for determining a time-averaged intensity value for the collected modulated electromagnetic radiation over time;

means for determining a modulation degree of the collected modulated electromagnetic radiation;

means for comparing the determined modulation degree of the collected modulated electromagnetic radiation with a control modulation degree measured at a previous time to detect the presence of bacteria; and means for indicating that bacteria are present in the determined modulation degree of the collected modulated electromagnetic radiation is significantly different from the control modulation degree measured at the previous time.

16. The apparatus of claim 15, further comprising means for determining an amplitude of the collected modulated electromagnetic radiation relative to the introduced modulated electromagnetic radiation.

17. The apparatus of claim 16, wherein the means for determining the amplitude of the collected modulated electromagnetic radiation relative to the introduced modulated electromagnetic radiation comprises a vector voltmeter for measuring the amplitude of the collected modulated electromagnetic radiation.

18. The apparatus of claim 17, wherein the means for determining the amplitude of the collected modulated electromagnetic radiation relative to the introduced modulated electromagnetic radiation further comprises a frequency translator for generating a frequency-shifted signal; the detector means comprises an avalanche photodiode to create a diode output signal, wherein the frequency-shifted signal is added to a bias voltage of the avalanche photodiode; and the vector voltmeter comprises a DC voltmeter for measuring a time-averaged value of the diode output signal.

19. The apparatus of claim 18, further comprising an alternating current voltmeter connected to the avalanche photodiode for creating an intermediate frequency output signal for determining the modulation degree of the collected modulated electromagnetic radiation.

20. The apparatus of claim 15, wherein the means for introducing modulated electromagnetic radiation comprises a laser.

21. The apparatus of claim 20, wherein the laser means comprises a diode laser and a signal source for generating a modulated signal to excite the laser diode.

22. The apparatus of claim 20 wherein the laser emits electromagnetic radiation at a wavelength between about 650 nm and 800 nm.

23. The apparatus of claim 15, wherein the processing means for determining the time-averaged intensity value for the collected modulated electromagnetic radiation over time comprises a multichannel plate photomultiplier for creating an output signal; and a voltmeter for measuring an amplitude of the output signal.

24. The apparatus of claim 15, wherein the processing means for determining the time-averaged intensity value for the collected modulated electromagnetic radiation over time comprises an avalanche photodiode excited by the collected modulated electromagnetic radiation to create a diode signal; and a DC voltmeter for measuring a magnitude of the diode output signal.

25. The apparatus of claim 15, wherein the presence of bacteria is detected in a plurality of samples, wherein the apparatus further comprises means for sequentially directing modulated electromagnetic radiation into each sample; means for sequentially introducing modulated electromagnetic radiation into each sample at a first point; and means for sequentially detecting the presence of bacteria in each of the plurality of samples.

26. The apparatus of claim 25, wherein the means for sequentially directing modulated electromagnetic radiation into each sample comprises a multiplexer connected to means for generating a modulated signal; and means for sequentially exciting a laser diode disposed adjacent each of the plurality of samples.

27. The apparatus of claim 26, wherein the processing means for determining the time-averaged intensity value for the collected electromagnetic radiation over time comprises a multichannel plate photomultiplier tube for creating an output signal.

28. The apparatus of claim 25, wherein the processing means for determining the time-averaged intensity value for the collected electromagnetic radiation over time comprises a plurality of detectors connected to a demultiplexer to create an output signal.

29. The apparatus of claim 25, wherein the means for sequentially directing modulated electromagnetic radiation into each sample comprises a signal source for transmitting a modulated driving signal to a laser to create modulated electromagnetic radiation; and an optical switch for sequentially transmitting the modulated electromagnetic radiation to each of the plurality of samples.

30. The apparatus of claim 29, wherein the processing means for determining the time-averaged intensity value for the collected electromagnetic radiation over time comprises a multichannel plate photomultiplier tube for creating an output signal; and a voltmeter for measuring an amplitude of the output signal.

31. The apparatus of claim 29, wherein the processing means for determining the time-averaged intensity value for the collected electromagnetic radiation over time comprises a plurality of detectors connected to a demultiplexer for creating an output signal; and a voltmeter for measuring an amplitude of the output signal.

32. Apparatus for detecting the presence of bacteria in a scattering and/or absorbing sample comprising:

means for introducing modulated electromagnetic radiation into the sample at a first point;

detector means for receiving collected modulated electromagnetic radiation at a second point;

means for determining a modulation degree of the collected modulated electromagnetic radiation;

means for comparing the determined modulation degree with a control modulation degree determined from a control sample known to be free of bacteria to detect the presence of bacteria; and means for indicating that bacteria if the determined modulation degree of the collected modulated electromagnetic radiation is significantly different from the control modulation degree of the control sample.

33. Apparatus for detecting the presence of bacteria in a scattering and/or absorbing sample comprising:

means for introducing modulated electromagnetic radiation into the sample at a first point;

detector means for receiving collected modulated electromagnetic radiation at a second point;

means for determining a phase shift of the collected modulated electromagnetic radiation;

means for comparing the determined phase shift with a control phase shift determined from a control sample known to be free of bacteria to detect the presence of bacteria; and means for indicating that bacteria are present if the determined phase shift of the collected modulated electromagnetic radiation is significantly different from the control phase shift of the control sample.

* * * * *